(12) United States Patent
Edelstam

(10) Patent No.: US 6,716,446 B2
(45) Date of Patent: Apr. 6, 2004

(54) MEDICAMENT AGAINST DYSMENORRHOEA AND PREMENSTRUAL SYNDROME

(75) Inventor: Greta Edelstam, Saltsjö-Duvnäs (SE)

(73) Assignee: Org. Nr. 556599-4968, Stockholm (SE)

( * ) Notice: Subject to any disclaimer, the term of this patent is extended or adjusted under 35 U.S.C. 154(b) by 0 days.

(21) Appl. No.: 10/211,050

(22) Filed: Aug. 2, 2002

(65) Prior Publication Data
US 2003/0004213 A1 Jan. 2, 2003

Related U.S. Application Data

(60) Division of application No. 09/785,149, filed on Feb. 16, 2001, now abandoned, which is a continuation of application No. 09/265,502, filed on Mar. 10, 1999, now abandoned, which is a continuation-in-part of application No. 08/800,737, filed on Feb. 15, 1997, now Pat. No. 5,977,143.

(51) Int. Cl.[7] ............ A61F 6/06; A61K 31/445; A61K 31/16; A01N 25/00
(52) U.S. Cl. ............ 424/430; 514/330; 514/626; 514/899
(58) Field of Search ............... 514/330, 626, 514/899; 424/430

(56) References Cited

U.S. PATENT DOCUMENTS 4,207,891 A * 6/1980 Bolduc ............ 128/235
4,780,480 A * 10/1988 Dunn ............ 514/469
5,534,242 A * 7/1996 Henry ............ 424/45

FOREIGN PATENT DOCUMENTS

WO    WO 98/56323    * 12/1998    ............ A61F/6/06

OTHER PUBLICATIONS

Narchi et al. CAPLUS Abstract, AN 1992:207278, 1992.*
Baker et al. Medline Abstract, AN 96069547, 1996.*
Bancroft e tal. Medline Abstract, AN 93234694, 1993.*
Doherty et al. Medline Abstract, AN 95200153, 1995.*

* cited by examiner

*Primary Examiner*—Shengjun Wang
(74) *Attorney, Agent, or Firm*—Rolf Fasth; Fasth Law Offices

(57) ABSTRACT

A local anesthetic is used for the manufacture of a medicament for use against dysmenorrhoea and premenstrual syndrome and for increasing fertility. A pharmaceutical composition may also be used that comprises a pharmaceutically effective dose of a local anesthetic together with a pharmaceutically acceptable excipient. The invention also relates to a process for using a catheter to pertubate the fallopian tubes to reduce dysmenorrhoea and premenstrual syndrome symptoms in a woman with the pharmaceutical composition that is intended to reach and exert an effect in the peritoneal cavity.

4 Claims, 6 Drawing Sheets

A

B

C

D

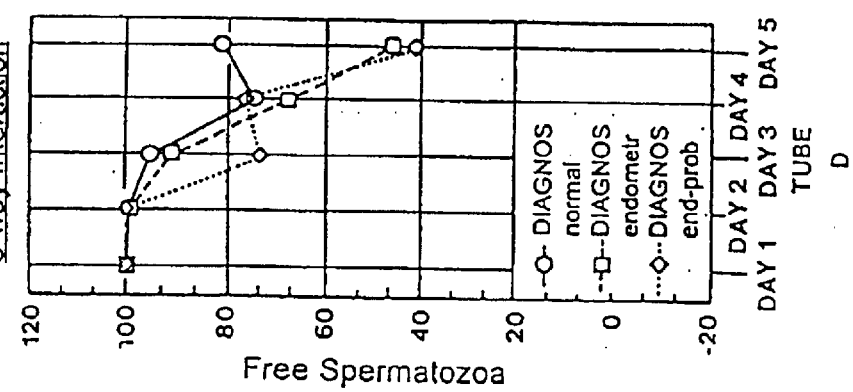
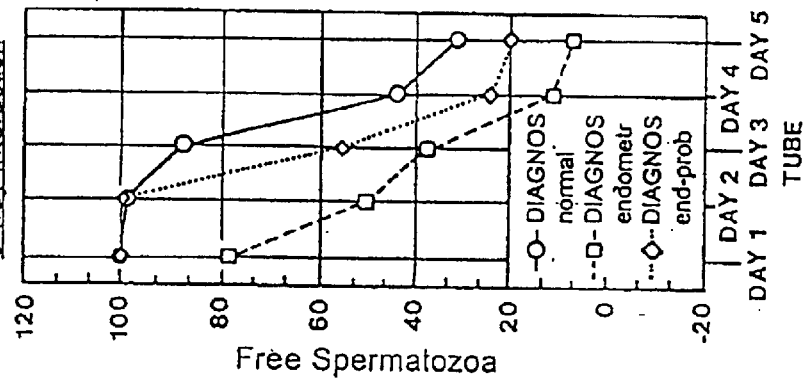
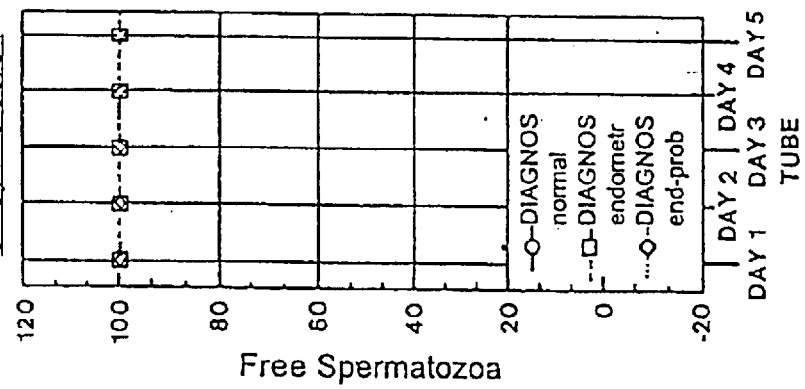
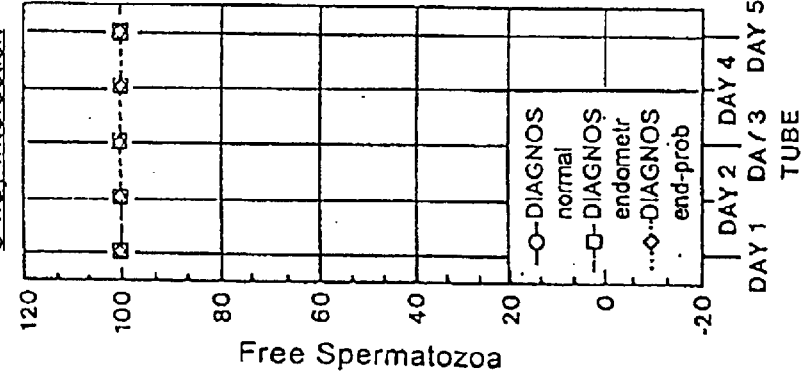

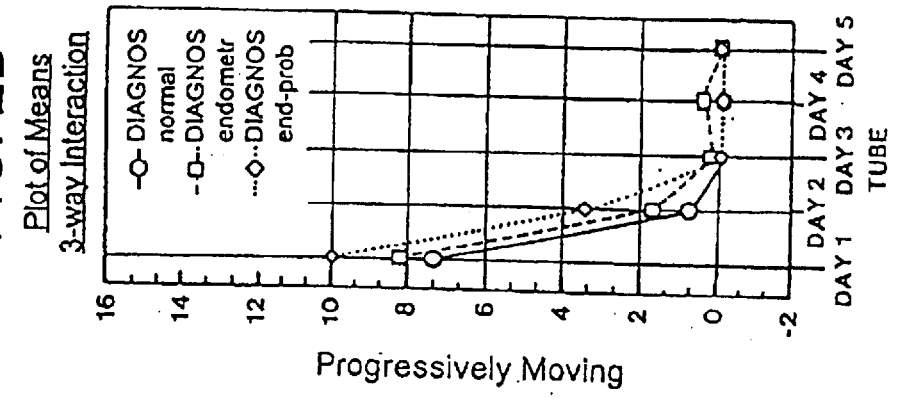
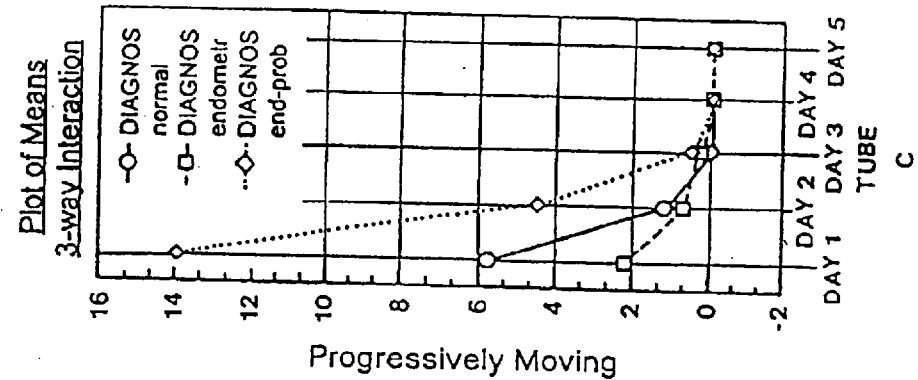
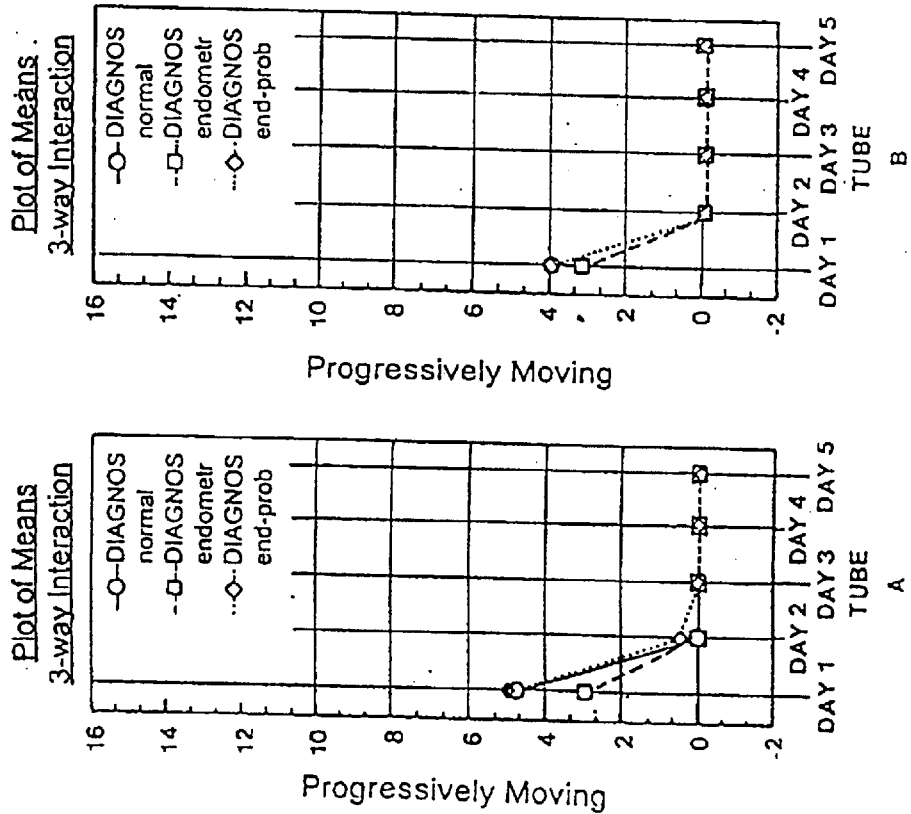

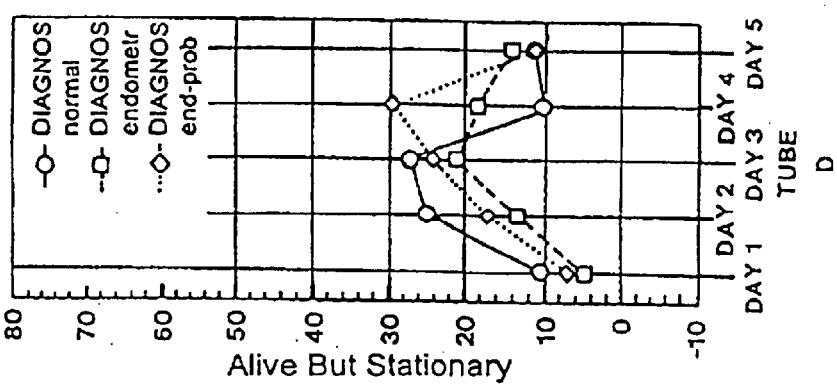
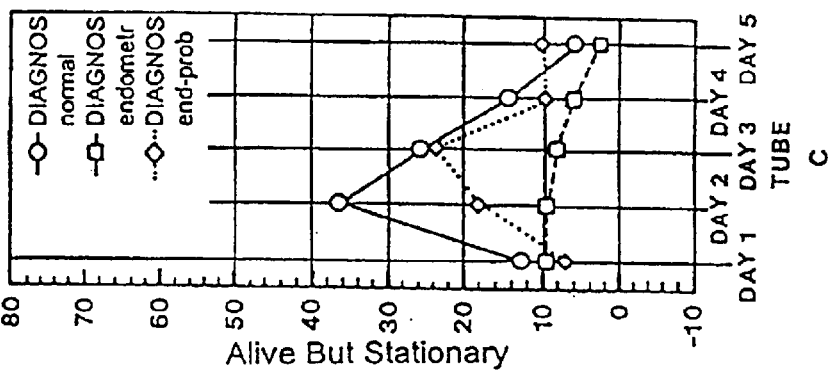
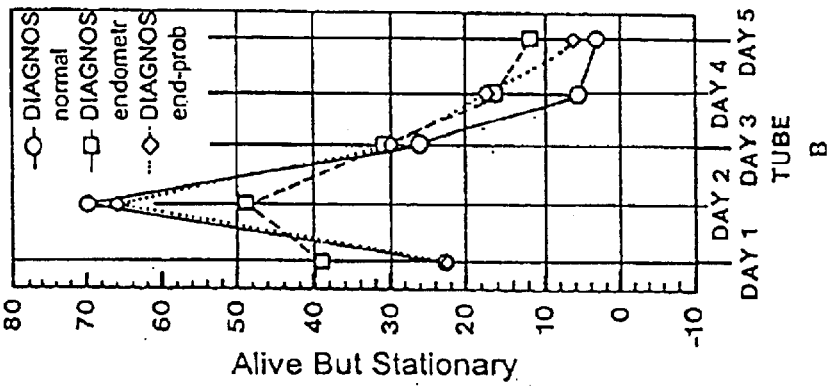
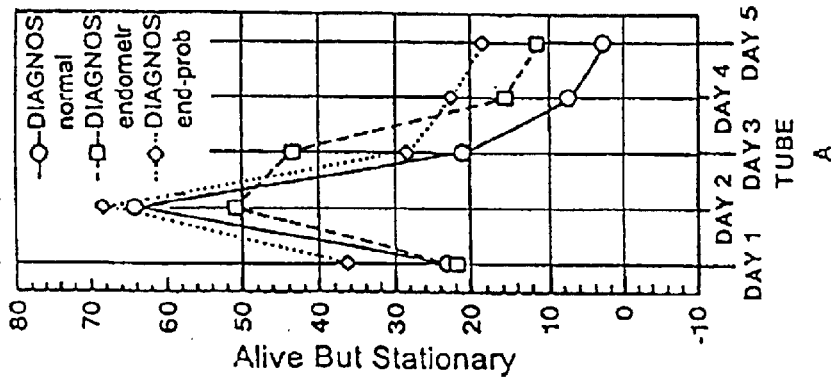

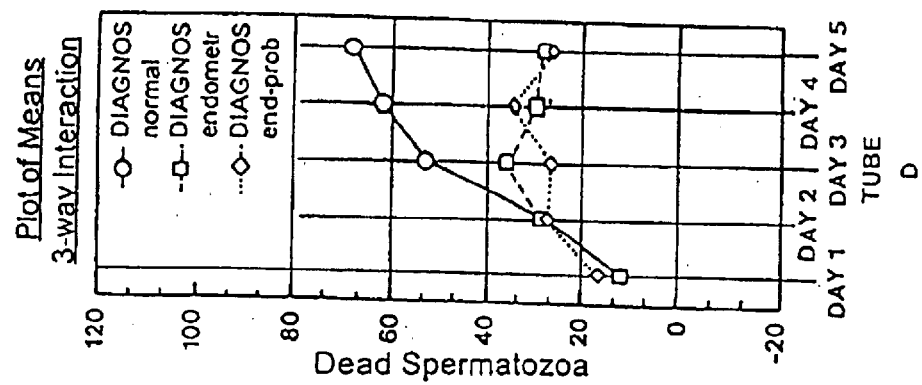
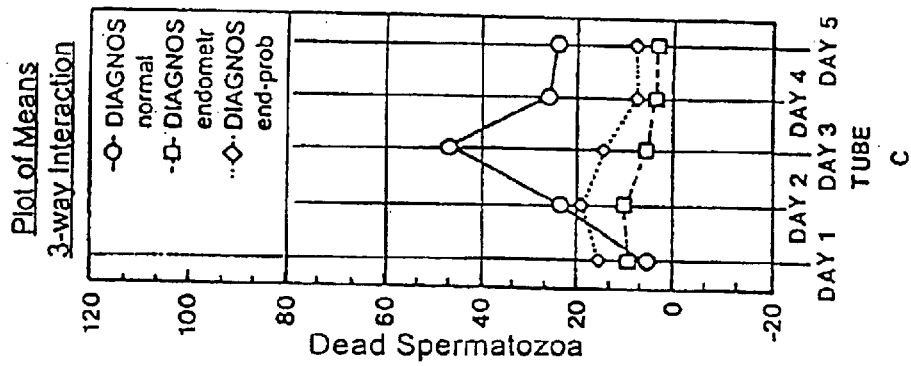
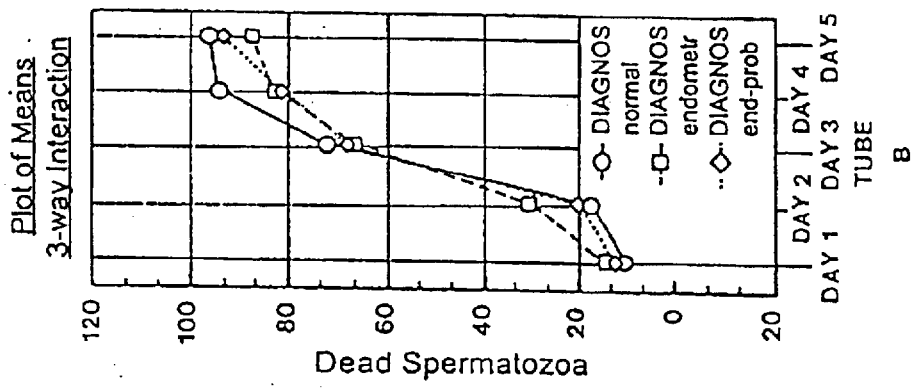
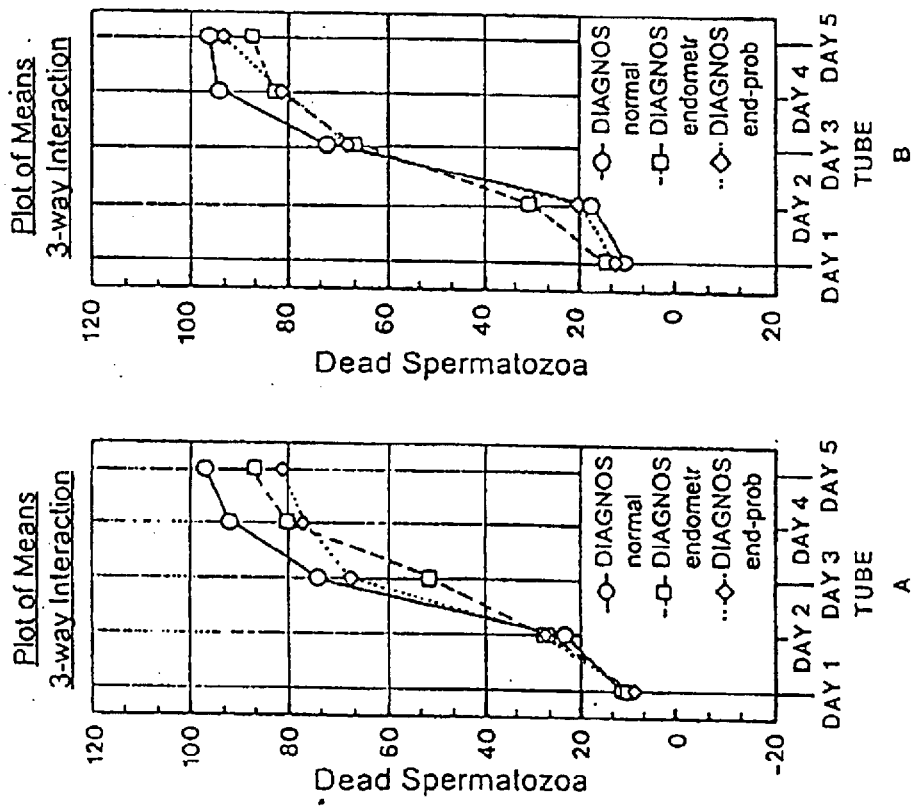

MEDICAMENT AGAINST DYSMENORRHOEA AND PREMENSTRUAL SYNDROME

PRIOR APPLICATION

This is a divisional application of U.S. patent application Ser. No. 09/785,149, filed Feb. 16, 2001, now abandoned; which is a continuation of Ser. No. 09/265,502, filed Mar. 10, 1999, now abandoned; which is a continuation-in-part application of U.S. patent application Ser. No. 08/800,737, filed Feb. 15, 1997, now U.S. Pat. No. 5,977,143.

TECHNICAL FIELD

The present invention relates to a method of using a medicament including a local anesthetic in a pertubation procedure for treating dysmenorrhoea and premenstrual syndrome.

BACKGROUND AND SUMMARY OF THE INVENTION

The causal relationship between reduced fertility and endometriosis without pelvic adhesions is not clear and neither is the lack of any improved fertility rate after the treatment. Women with endometriosis also suffer from various degrees of dysmenorrhoea and increased occurrence of premenstrual syndrome (PMS). An increased number of leukocytes has been shown in the peritoneal fluid from patients with endometriosis peritoneal implants and has been considered as an ongoing sterile inflammation. Peritoneal fluid macrophages in women with endometriosis may have an increased capacity to resist apoptosis (programmed cell death) and continue to survive which might be crucial for the fertility. Furthermore, phagocytosis of spermatozoa has been found to be increased during incubations for 24 hours in vitro with the peritoneal fluid from patients with endometriosis. It should be noted that endometrium, i.e., the normal mucosa in the uterine cavity, is not the same as endometriosis cells, i.e., endometrium-like cells that grow as a pathological process in the peritoneal cavity or in other locations outside the uterine cavity, that may be cultivated in-vitro as cell lines.

Infertility or sub-fertility is often a dramatic problem for people afflicted therewith. A common treatment of infertile women is IVF (in vitro fertilization) treatment. The basis of the IVF treatment is as follows:

Stimulation of ovulation: Daily hormonal injections, ultrasound examinations and blood samples;

Oocyte retrieval: Ultrasound guided ovarian punctures performed vaginally in local anesthesia;

Preparation of spermatozoa: Swim-up, swim-down, sperm select or other methods to select the optimal population with the best progressive motility;

In vitro fertilization: Incubation of oocytes and the selected population of spermatozoa in a cell incubator. Direct microscopic inspection of cell division and selection of the most vital blastocyte; and Embryo transfer: 2–3 blastocytes with the best viability is deposited in the uterine cavity for hopeful implantation in the endometrium.

IVF treatment is an expensive method that for some couples initiates complicated psychological side effects. The technical and artificial way of trying to become pregnant has the disadvantages for couples going through the treatment which may adversely affect the relationship. After all the troublesome treatment there is only a pregnancy rate of about 25–30%, leaving those who did not succeed with a damaged relationship and still no child. The cost for IVF treatment is around 20,000–30,000 SEK per menstrual cycle.

In spite of several previous investigations, the reasons for infertility during endometriosis have not been established and neither has the lack of improved fertility rate after treatment. Particularly the relationship is unclear between mild endometriosis and sub-fertility in the absence of pelvic adhesions.

The increased number of leukocytes contained in vivo primed macrophages secreting a macrophage derived growth factor (MDGF) that may explain the proliferation of the endometriosis tissue. Other secretory products from the macrophages, growth factors such as TNF and interferon, exhibit gamete toxicity and may also have an adverse impact on the fertility process.

Also, the cell-free peritoneal fluid is of importance in the reduced fecundity since it has been shown that it significantly reduces the ovum pick-up capacity of the fimbriae of the fallopian tubes. In the peritoneal fluid from patients with endometriosis and unexplained infertility, a reduced progressive velocity of spermatozoa has been found. Even more interesting is the increased phagocytosis of spermatozoa that has been found during incubations for 24 hours in vitro with peritoneal fluid from patients with endometriosis. In that particular study there were, however, several different sperm donors and therefore immunological factors involved cannot be excluded.

The present invention is an alternative method to the IVF treatment for increasing fertility and is also a method for reducing dysmenorrhoea and premenstrual syndrome of women. It has been found by in vitro studies that phagocytosis of spermatozoa is reduced by lidocaine. It is suggested that this effect of lidocaine is due to stabilization of the cell membrane by prohibiting the increase of $Na^+$ permeability and interference with ATP in the cell membrane. The cost for this new fertility treatment will be approximately 10% of the IVF treatment, e.g., 2,500 SEK per menstrual cycle. The method of the present invention has no technical fertilization process that may cause psychological side effects. This treatment can be tried in patients with endometriosis and/or unexplained infertility. It can be carried out while waiting for IVF treatment and does not affect the possibility of successful later IVF treatment.

So far no treatment of infertility with lidocaine is reported in the literature. However, other pharmaceutical effects of lidocaine are known, e.g., as in EP 507 160, which discloses an external preparation for application to the skin containing and lidocaine which comprises a drug-retaining layer placed on a support. The preparation should be used for treatment of herpes zoster neuralgia and postherpetic neuralgia.

More particularly, the present invention relates to a pertubation method of using a local anesthetic that may be used as a treatment against dysmenorrhoea and premenstrual syndrome and for increasing fertility. A pharmaceutical composition may also be used that comprises a pharmaceutically effective dose of the local anesthetic together with a pharmaceutically acceptable excipient.

BRIEF DESCRIPTION OF THE DRAWINGS

As used in the drawings endometr relates to endometriosis and end-prob relates to probable endometriosis.

FIG. 1 is a schematic illustration showing the number of free spermatozoa shown for each day of incubation: with cell medium (A, control), with cell medium and lidocaine (B), with peritoneal fluid (C, control) and with peritoneal fluid and lidocaine (D);

FIG. 2 is a schematic illustration showing the number of progressively moving spermatozoa shown for each day of incubation: with cell medium (A, control), with cell medium and lidocaine (B), with peritoneal fluid (C, control) and with peritoneal fluid and lidocaine (D);

FIG. 4 is a schematic illustration showing the number of alive but stationary spermatozoa shown for each day of incubation: with cell medium (A, control), with cell medium and lidocaine (B), with peritoneal fluid (C, control) and with peritoneal fluid and lidocaine (D);

FIG. 5 is a schematic illustration showing the number of dead spermatozoa shown for each day of incubation: with cell medium (A, control), with cell medium and lidocaine (B), with peritoneal fluid (C, control) and with peritoneal fluid and lidocaine (D);

DETAILED DESCRIPTION

Figure 3A:
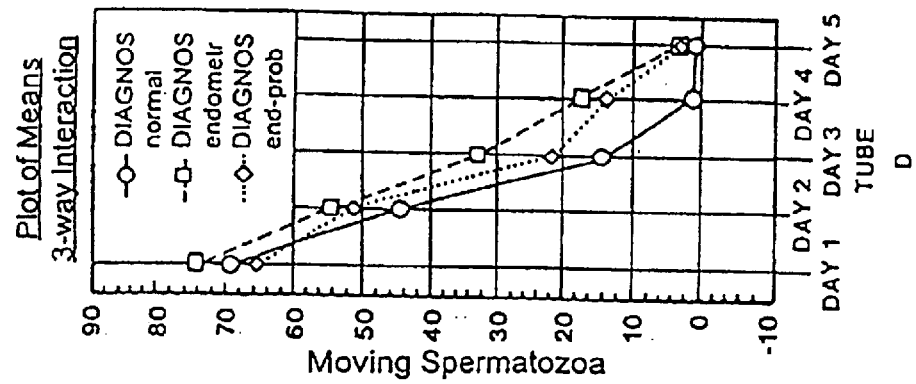
FIG. 3 is a schematic illustration showing the number of non-progressive but moving spermatozoa shown for each day of incubation: with cell medium (A, control), with cell medium and lidocaine (B), with peritoneal fluid (C, control) and with peritoneal fluid and lidocaine (D)
Figure 3B:
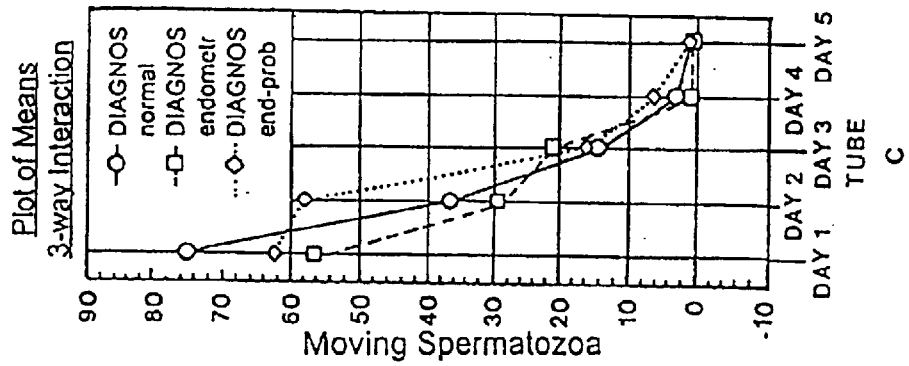
Figure 3C:
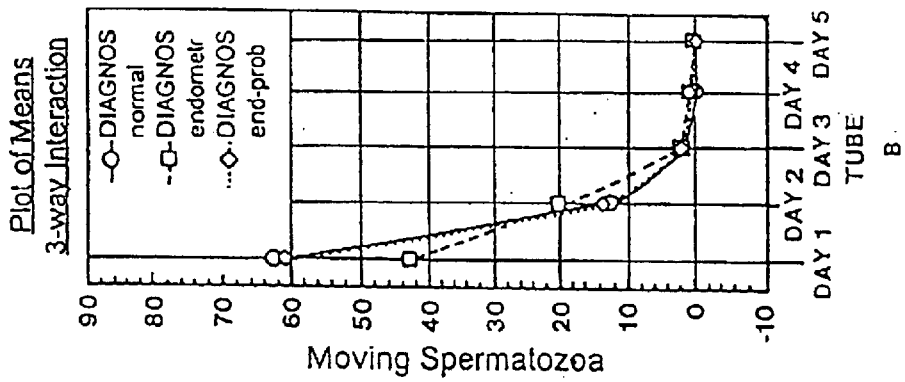
Figure 3D:
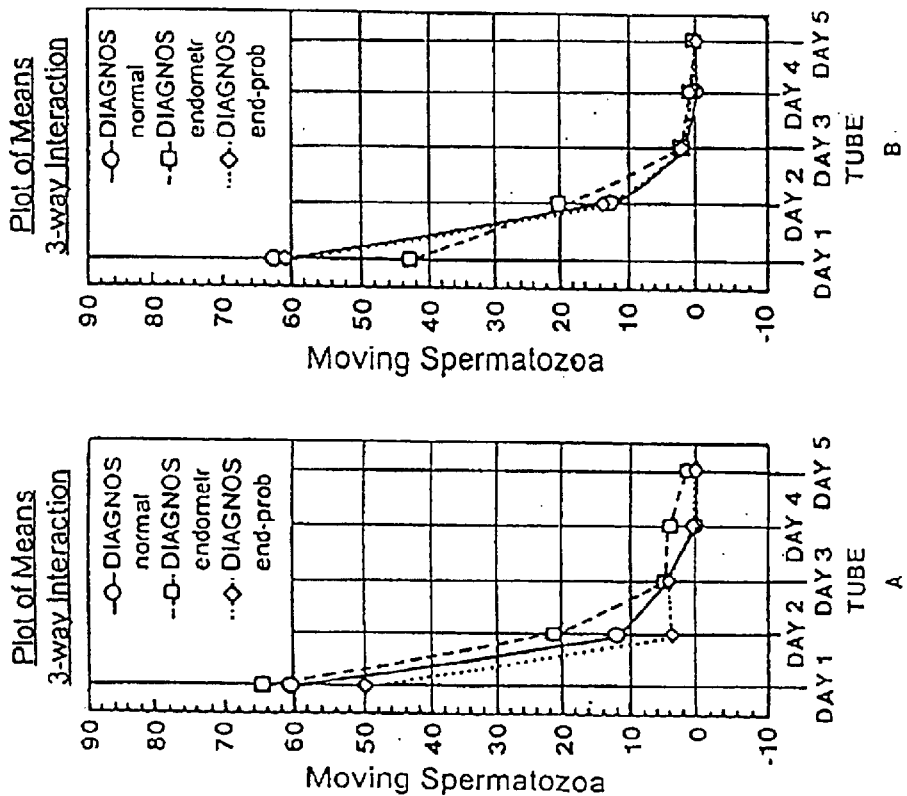

With reference to FIGS. 1–5, the use of a local anesthetic for the manufacture of a medicament for use against infertility or for increasing fertility. The medicament may also be used in a pertubation method as a treatment against dysmenorrhoea and PMS. The local anesthetic may be selected from any substance that has a local anesthetic effect. Examples of such substances are bupivacaine (1-butyl-N-(2,6-dimethylphenyl)-2-piperidine-carboxamide), lidocaine (2-(dicthylamino)-N-(2,6-dimethylphenyl)acetamide), mepivacaine (N-(2,6-dimethylphenyl)-1-methyl-2-piperidinecarboxamide), prilocaine (N-(2-methylphenyl)-2-(propylamino)propanamide) and ropivacaine ((S)-N-(2,6-dimethylphenyl)-1-propy-2-pipendinecarboxamide). Other local anesthetics could also be used. Preferably, lidocaine is used.

The composition is preferably administered in the peritoneal cavity, preferably by pertubation. The pertubation method is a method of slowly passing a fluid through an existing biological pathway, such as the fallopian tubes. A catheter equipped with an inflatable cuff in order to make the fluid move forwardly without any retrograde leakage back out the biological pathway, is introduced through a vagina into a cervix of a uterus. One intention with the treatment is using the catheter to pass the fluid through the genital tract and the fallopian tubes and into the peritoneal cavity. The concentration of the effective substance is at least 5 microgram/ml. One may use 100–2000 micrograms in 1–20 ml, preferably about 118 micrograms. The dose that is administrated is at least 100 micrograms and preferably about 1000 micrograms.

The active substance or compound may be mixed with an excipient which is pharmaceutically acceptable and compatible with the active ingredient and in amounts suitable for use in the therapeutic methods described herein. In addition, if desired, the composition can contain minor amounts of auxiliary substances such as wetting or emulsifying agents, pH buffering agents and the like which enhance the effectiveness of the active ingredient.

The pharmaceutical composition of the present invention may include pharmaceutically acceptable salts of the components herein. Pharmaceutically acceptable salts include the acid addition salts that are formed with inorganic acid such as, for example, hydrochloric or phosphoric acids, or such organic acids as acetic, tartaric and mandelic acid.

Physiologically tolerable carriers may also be used. Exemplary of liquid carriers are sterile aqueous solutions that contain no materials in addition to the active ingredients and water or contain a buffer such as sodium phosphate at physiological pH value, physiological saline or both, such as phosphate-buffered saline. Furthermore, aqueous carriers may contain more than one buffer salt, as well as salts such as sodium and potassium chlorides, dextrose, propylene glycol, polyethylene glycol and other solutes.

The composition may also comprise hyaluronan which is a viscous substance, e.g., in gel formate. Hyaluronan gives a slow release of the active substance which is preferable as conception may take place up to 24 hours after ovulation and the treatment according to the present invention. Another advantage is that hyaluronan has a stimulating effect on the sperms.

Infertility is generally not being considered as an illness. The present invention also embraces a process for treating infertility in a woman with a pharmaceutical composition according to the present invention and may be characterized in that the pharmaceutical composition is inserted by pertubation.

The present invention especially relates to a pharmacologically therapeutic fertility treatment against infertility or for increasing fertility wherein: a) an ovulation in progress is diagnosed; and b) a treatment with a local anesthetic is performed when ovulation is expected according to step a).

The treatment is preferably performed by pertubation. Preferably, the steps are as follows:

Spontaneous ovulation: Primary treatment during normal menstrual cycle. Stimulation only in anovulatory patients and primary with Clomiphene (tablets) which is easy and inexpensive. One blood sample is needed post-ovulatory to confirm that there has been an ovulation during the treated cycle.

LH (luteinizing hormone) test: The LH-surge 24–36 hours prior to ovulation is diagnosed by a self test at home of urine sample.

Pertubation: When the LH-test is positive a pertubation treatment is given with, e.g., 10 ml of 100 micrograms/ml lidocaine in physiological NaCl or Ringer-solution during a normal gynecological examination. No anesthesia is needed.

Fertilization: No artificial treatment. The couple will try and achieve pregnancy by normal way by coitus at home after the pertubation treatment is given.

This absence of adverse effects on sperm survival demonstrates that the spermatozoa are unaffected by lidocaine which has also been demonstrated in other studies. It seems to be the case also for the oocytes since high levels of lidocaine have been measured in vivo without any problems with fertilization or embryo development. The highest levels were 118 micrograms/ml which means that the dose of 1000 micrograms of lidocaine given in the in vitro incubations ought to be able to be used diluted to, e.g., 100 micrograms/ml in 10 ml of isotone fluid. This concentration has been used for a clinical study of pregnancy outcome after pertubation carried out 24 hours preovulatory to increase sperm survival.

Lidocaine has been used for many years without any reports of adverse effects during pregnancy and has also been shown in an animal study and should therefore be possible to use for treatment of infertility in the endometriotic patient.

The invention may be illustrated by the following example. All technical and scientific terms used are, unless otherwise defined, intended to have the same meaning as commonly understood by one of ordinary skill in the art.

EXAMPLE 1

Reduction of Phagocytosis of Spermatozoa in PF (Peritoneal Fluid) from Women with Endometriosis.

This study was undertaken to further analyze the function of the leukocytes on the reduced fertility during endometriosis and also search for a potential therapeutic approach. To exclude immunological influences only one sperm donor was participating in the experiments. Prepared sperm samples were incubated with non-centrifuged peritoneal fluid from healthy women and women with endometriosis to evaluate the importance of phagocytosis of spermatozoa on the reduced fecundity during endometriosis. The number of viable spermatozoa in the incubations were counted daily for five days with or without the presence of local anesthetics that was added in search of a method to reduce the activity of the peritoneal leukocyte populations.

The patients were divided into three different groups. The control material (n=9, mean age=38.5 years) consisted of women going through laparoscopic sterilization or women with unclear abdominal pain. The control cases had laparoscopic findings considered as normal with anatomically normal uterus and fallopian tubes.

The study group were women going through laparoscopy to find the cause of infertility or of abdominal pain and where the diagnosis was endometriosis (n=11, mean age=34.5 years). In this group the diagnose was laparoscopic in 8 patients and anamnestic probable endometriosis in 3 patients but who had not yet developed any endometriosis implants that could be seen at the laparoscopy.

The sperm donor was a healthy 38 year old male with normal fertility with an continence period of 2–3 days before each sperm sample. The sperm samples were prepared by the swim up technique to select the optimal population.

After the patients had been anaesthetized, blood samples were taken for later analyses. At the beginning of the laparoscopy with the instruments safely in the abdominal cavity, all obtainable peritoneal fluid in the Douglas' pouch was aspirated by a suction unit through a Teflon catheter (diameter 1.7 mm, Optinova, Godby, Finland) and mixed with 10 IU of Heparin/ml in a Teflon bottle and immediately taken care of. The amount of peritoneal fluid were determined by weighing on an electric balance. Teflon was the material of choice for collecting the peritoneal fluid due to its low adhesion of mammalian cells. Heparin was used as anticoagulant to prevent the leukocytes from aggregating. Previously citrate has been used which in the sperm incubation had adverse effects on sperm viability. All samples were taken after permissions from the patients and the sampling procedure was approved by the Ethical Committee, Faculty of Medicine, Uppsala University, Sweden.

Teflon vials were used for all incubations that were done in a humid cell incubator as follows:

a) Cell medium (1 ml), spermatozoa ($10^6$ in 1 ml cell medium) and 0,1 ml NaCl;

b) Cell medium (1 ml), spermatozoa ($10^6$ in 1 ml cell medium) and 0,1 ml lidocaine 10 mg/ml (Xylocain, ASTRA);

c) Spermatozoa ($10^6$ in 1 ml cell medium), peritoneal fluid (1 ml) and 0,1 ml NaCl; and d) Spermatozoa ($10^6$ in 1 ml cell medium), 0,1 ml lidocaine (10 mg/ml) and peritoneal fluid (1 ml).

Earls cell medium (Sigma) with 0.35% BSA (bovine serum albumin). The remaining amount of peritoneal fluid was centrifuged and the supernatant frozen (−20 C.) for subsequent analyses of hyaluronan. In the peritoneal fluid, the concentration of hyaluronan can be used as a marker of ongoing inflammation to exclude a PID (pelvic inflammatory disease). The vials were analyzed daily during five days and the following was counted in all the A-D incubations up to 100 spermatozoa:

Number of free spermatozoa non-adherent to leukocytes;
Number of spermatozoa with progressive motility;
Number of spermatozoa with non-progressive movement;
Number of spermatozoa that are stationary and alive; and
Number of dead spermatozoa.

Also, the percentage of viable peritoneal leukocytes were noted daily with the use of Trypan blue. The main finding was that there were statistically significantly less phagocytized spermatozoa ($p<0.02$) in the vials when incubated with peritoneal fluid and lidocaine. The spermatozoa were observed caught in large aggregates of leukocytes and some apparently undergoing phagocytosis thus reducing the number of free functioning spermatozoa.

After two days of incubation there where statistically significantly more free spermatozoa in the incubations with peritoneal fluid from the normal group compared to the group with endometriosis (Kruskal Wallis $p<0.014$). No adverse effects were found on sperm survival and there were statistically no significantly differences between the incubations of spermatozoa with or without lidocaine after 24 or 48 hours. The p-values using Wilcoxon are shown in Tables I and II, respectively.

The progressive motility is reduced more rapidly without the presence of peritoneal fluid, as shown in FIG. 2, compared to the incubation of spermatozoa alone. In the presence of peritoneal fluid and lidocaine there were significantly more free spermatozoa, especially after two days incubations in the endometriosis group, as shown in FIG. 1 and Table II. There were more dead spermatozoa in incubations with lidocaine over time in both diagnosis groups, as shown in FIG. 5 and Table II. Hyaluronan concentrations in peritoneal fluid exhibited no indications of ongoing inflammatory process.

TABLE 1

P-values for the different parameters registered in the incubations when comparing with or without incubation with lidocaine. Data after 24 hours incubation time.

| | Spermatozoa ± lidocaine | Spermatozoa + PF Normal, ± lidocaine | Spermatozoa + PF, endometr. ± lidocaine | All patients without concern of diagnosis ± lidocaine |
|---|---|---|---|---|
| free, non-adherent to leukocytes | — | All free with and without lidocaine | 0.59 | 0.27 |
| progressively moving | 0.88 | 0.046 (a) | 0.67 | 0.11 |
| non-progress. movement | 0.59 | 0.59 | 0.79 | 0.58 |
| stationary | 0.76 | 0.40 | 0.31 | 0.18 |
| immobile (dead) | 0.28 | 0.14 | 0.09 | 0.024 (b) |

TABLE 1-continued

P-values for the different parameters registered in the incubations when comparing with or without incubation with lidocaine. Data after 24 hours incubation time.

| | Spermatozoa ± lidocaine | Spermatozoa + PF Normal, ± lidocaine | Spermatozoa + PF, endometr. ± lidocaine | All patients without concern of diagnosis ± lidocaine |
|---|---|---|---|---|
| Leukocyte viability | — | 0.26 | 0.29 | 0.92 |
| Spermatozoa adherent to leukocytes | — | No adherent to leukocytes in either group | 0.68 | 0.80 |

(a) more progressively moving spermatozoa in the incubations without lidocaine.
(b) more dead in the lidocaine group

TABLE II

P-values for the different parameters registered in the incubations when comparing with or without incubation with lidocaine. Data after 48 hour incubation.

| | Spermatozoa ± lidocaine | Spermatozoa + PF, Normal, ± lidocaine | Spermatozoa + PF, endometr. ± lidocaine | Spermatozoa + PF without concern of diagnosis ± lidocaine |
|---|---|---|---|---|
| free, non-adherent to leukocytes | — | 1.0 | 0.018 (d) | 0.0021 (d) |
| progressively moving | No progressively moving with or without lidocaine | 1.00 | 0.89 | 0.95 |
| non-progress. movement | 0.18 | 0.025 (c) | 0.21 | 0.021 (c) |
| stationary | 0.78 | 0.26 | 0.58 | 0.22 |
| immobile (dead) | 0.50 | 0.038 (c) | 0.003 (c) | 0.00025 (c) |
| Leukocyte viability | — | 0.78 | 0.51 | 0.57 |
| Spermatozoa adherent to leukocytes | — | 1.00 | 0.53 | 0.63 |

(c) more in lidocaine
(d) more free in the lidocaine group

This investigation includes the effect of lidocaine on sperm survival and effect on the peritoneal leukocyte phagocytosis of spermatozoa in vitro during incubation for five days. This study has included only one donor of spermatozoa to avoid different immunological combinations which would have been uncontrolled factor in the experiments. Also this study follows the sperm survival for up to 5 days whereas previous studies have investigated the sperm survival during a 24 hour period. Furthermore, not only the number of free non-phagocytized spermatozoa was counted but also how many exhibited progressive or stationary movement as well as the number of alive, dead or free (i.e., not adhered to leukocytes) spermatozoa.

It was confirmed that the reduced fertility in endometriosis patients was due to sperm phagocytosis. Increased phagocytosis capacity of peritoneal macrophages from patients with endometriosis has also been demonstrated with fluorescent beads.

Other studies of sperm phagocytosis have not considered the problem with loss of leukocytes that adhere to some material more than other. Glass containers have been used for storage of peritoneal fluid. Glass has the highest adhesions of leukocytes and has been used for separating macrophages. Polypropylene was chosen which is a better alternative than glass concerning the cell adhesions problem but less optimal than Teflon.

The finding of more dead spermatozoa in incubations with lidocaine over time must be considered as an effect of the reduced sperm phagocytosis in the presence of lidocaine, since there were, in incubations of spermatozoa alone with or without lidocaine, no adverse effects found on the spermatozoa. This may also be the explanation for the finding of increased non-progressively moving spermatozoa in the lidocaine incubations, as best shown in FIG. 3. The reduction of progressive motility without the presence of peritoneal fluid might be an indication of that the peritoneal fluid contains substances necessary for the spermatozoa to maintain their function.

The fimbriae of the fallopian tubes are constantly moistured by peritoneal fluid which in the case of patients with endometriosis reduces the capacity of ovum pick-up. As demonstrated in this study, the leukocytes in the peritoneal fluid of patients with endometriosis are more potent in phagocytizing spermatozoa. Thus, women with endometriosis can have two factors contributing to their reduced fertility. This study has also indicated the possibility of using the effect of lidocaine in order to reduce the phagocytosis of spermatozoa.

In summary, this study has demonstrated a reduced phagocytosis of spermatozoa in the presence of lidocaine. This phenomenon has to be followed up with randomized clinical trials of pertubations with saline or lidocaine/saline solutions preovulatory (LH-surge time).

A study has been undertaken to analyze further the spermatozoa-leucocyte interaction in patients with endometriosis and to find a potential therapeutic approach. To exclude immunological influences only one sperm donor was used. Phagocytosis and sperm viability were assessed during incubations in peritoneal fluid from healthy women and women with endometriosis. The incubations were carried out with or without the supplementation of lignocaine which was chosen due to its previously documented cell membrane stabilizing effect. Thus, the hypothesis was that lignocaine could block the phagocytosis of spermatozoa and incubations were therefore made of the spermatozoa with non-centrifuged peritoneal fluid, i.e., containing phagocytes. Lignocaine was added to assess the effect on the spermatozoa alone in the cell medium as well as the effect on the phagocytes in the peritoneal fluid. Samples from the incubations were studied daily and the number of viable and dead spermatozoa were counted. The number of free spermatozoa, not adhered to leukocytes, was significantly increased when incubated in human peritoneal fluid supplemented with lignocaine. Thus, lignocaine contributes to increasing the number of free spermatozoa and maintaining the possibility of fertilizing an oocyte.

The administration of the active substances and compounds may be performed in a variety of ways. The active compounds may include, but are not limited to, local anesthetics, physiological saline, Ringer solution, air and fat emulsions. For example, a small sterile thin catheter for hysterosonosalpingography is inserted through the cervix and into the uterine cavity. The catheter may be held by a sterile tool before the catheter is inserted. It is important that the equipment and the active substance intended to pass through the cervix are sterile to avoid genital tract infections. A small rubber cuff or intraluminal rubber balloon on the catheter is inflated with saline to prevent retrograde leakage. The fluid may then be infused through the uterine cavity and pertubated through the fallopian tubes into the peritoneal cavity to be deposited in the peritoneal cavity. About 10–20 ml of fluid may be used which means that the fluid has to flow through the uterine cavity which contains 1–3 ml, flood through the fallopian tubes and finally having at least 7 ml reaching the free peritoneal cavity since the uterine cavity contains only 1–2 ml. There should be no pressure used or needed since the passage has to be open through the fallopian tubes. The fluid has normal room temperature, but can also be of body temperature. The rubber cuff is then deflated and the catheter is thereafter removed by pulling out the catheter from the uterine cavity and vagina. The procedure takes a couple of minutes to complete.

The procedure with pertubation has empirically turned out to reduce menstrual pain (dysmenorrhoea) and PMS (premenstrual syndrome). This may be due to a direct or indirect local effect of local anesthetics (e.g., lignocaine) reducing the endometriosis implants deposited in the peritoneal cavity or depressing the hormonal activity in the ovaries. Additionally, the reduced dysmenorrhoea and PMS may be due to a mechanical effect of removing mucous plugs or intra-fallopian minor adhesions around endometriosis implants. Another factor may be the mechanical effect of the hormonal change due to the improved mechanical flow through the fallopian tubes that could increase the hormonal drainage of peritoneal fluid from the cavity to the uterine cavity. This unexpected reduction of menstrual pain and the PMS from the patients who have been treated with pertubation is new and not described earlier.

It was noted in the group of women participating in the study that the pertubation procedure itself increased the overall pregnancy rate for the women with endometriosis. Pertubation is a procedure that is normally carried out during X-ray examination of the fallopian tubes. For example, pertubation is often used as a diagnostic method in connection with ultrasound or X-ray contrast fluids for visualizing patent or closed fallopian tubes.

By using the pertubation method of the present invention, an overall pregnancy rate of 30% was unexpectedly noted in contrast to the natural pregnancy rate for women with endometriosis that is less than 5%. Additionally, an interesting and unexpected side effect that has been noted in the group of women treated is the reduction of menstrual pain (dysmenorrhoea) and premenstrual symptom (PMS). Reduced dysmenorrhoea was found in 32% of those patients suffering from dysmenorrhoea after the above described pertubation treatment had been carried out. Similarly, reduced PMS was found in 30% of those patients suffering from PMS. These side effects may have the following potential explanations:

The mechanical effect of the pertubation procedure, i.e., cleaning of the fallopian tubes and increasing the hormonal uptake from the peritoneal fluid into the uterus and reducing the serum levels and thereby the PMS symptoms;

The local beneficial effect of local anesthetics and reduction of inflammatory and/or hormonal activity and thereby reduction of the pain and the PMS;

The regressive effect directly on the endometriotic implants; and

The effect of a combination of two or more of the effects mentioned above.

It was expected that the lignocaine pertubation treatment would reduce phagocytosis of the spermatozoa but this turned out not to be the main finding of the study. An important finding was that the reduced dysmenorrhoea and PMS could be the regression of endometriosis when taking into account the reduced menstrual pain and increased pregnancy rate after the initial six pertubation treatments were completed. For those patients who noticed reduced dysmenorrhoea but did not become pregnant, the reduced pain level lasted around one year. This indicates that the lignocaine pertubation method of the present invention is distinctly different from conventional short term (hours) effect of topical or subcutaneously injected local anaesthesia.

The pertubated lignocaine may have a direct effect on the undesirable endometriosis implants. The pertubated lignocaine may reduce the activity of the endometriosis implants. For example, the leukocytes (white blood cells) release inflammatory mediators/cytokines that are reduced/blocked by the pertubated lignocaine that is deposited in the peritoneal cavity. More particularly, the pertubated lignocaine may have an anti-inflammatory effect and stabilize and block the cell membranes to prevent the increase of $Na^+$ permeability and interference with ATP of the blood cells. In this way, the release of the inflammatory substances from the leukocytes is dramatically reduced. The lignocaine compound also fills/flushes the uterus and the fallopian tubes since the amount of the compound far exceeds the volume of the uterus cavity.

Figure 7:
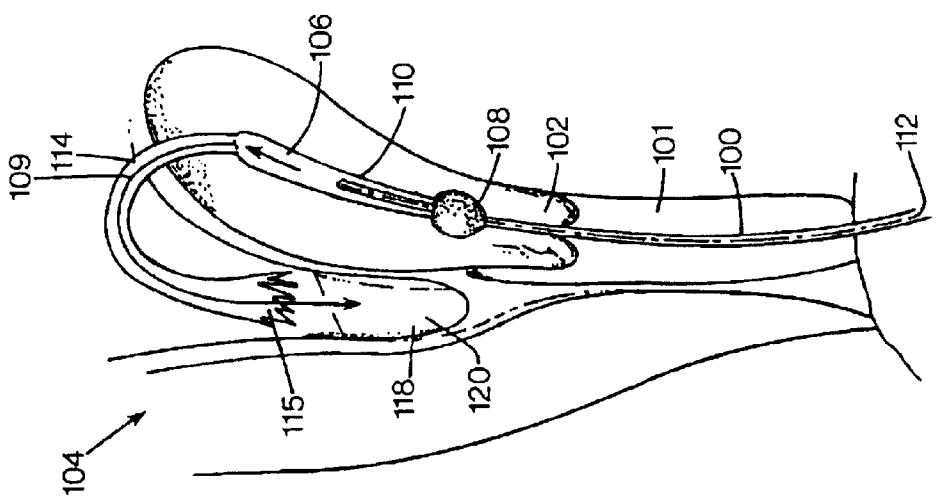
FIG. 7 is a cross-sectional side view of the catheter inserted through the cervix of the woman.
Figure 6:
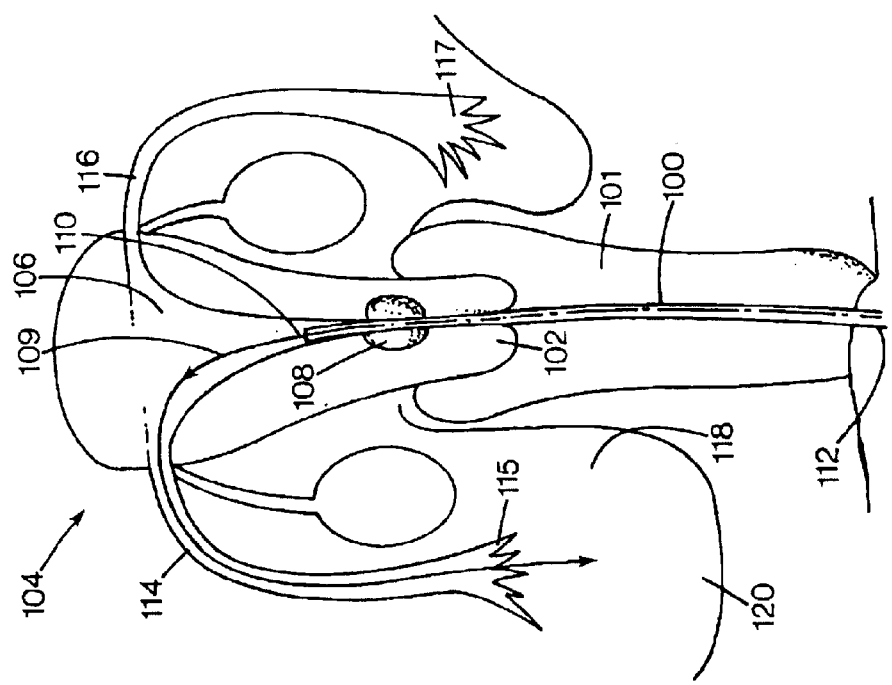
FIG. 6 is a cross-sectional front view of a catheter inserted through the cervix of a woman.

With reference to FIGS. 6–7, a sterile catheter 100 is inserted through a vagina 101 and through a cervix 102 of a woman 104 and into a uterine cavity 106. During the insertion, the catheter 100 is held with a sterile tool or glove to ensure the catheter remains sterile during the insertion step. The catheter 100 has a sterile inflatable cuff 108 that is collapsed when the catheter 100 is inserted into the uterine cavity 106. When an outer end 110 of the catheter 100 is disposed inside the uterine cavity 106, the cuff 108 is inflated with a suitable liquid to prevent any undesirable back-flow down through the cervix 102.

A suitable sterile composition, as indicated by an arrow 109, is injected through the catheter 100, such as by using a sterile syringe connected to an application end 112 of the catheter. As mentioned above, the composition may include a local anesthetic, such as lidocaine. About 10–20 ml of the active composition is injected through the application end 112 and flows out through the outer end 110 disposed inside the uterine cavity 106. Because the volume of the active substance 109 is substantially greater than the volume of the uterine cavity 106 and fallopian tubes 114, 116, the composition fluid 109 not only fills the uterine cavity 106 but also pertubates or flows into the fallopian tubes 114, 116, out through fimbriae, i.e., the open end of the fallopian tubes 115, 117, respectively, and into a peritoneal cavity 118.

In this way, the fluid 109 may flush the uterine cavity 106 and the fallopian tubes 114, 116 and be deposited at a bottom pouch of Douglas 120 of the peritoneal cavity 118. The composition fluid 109 may then reduce the effect of leukocytes and endometriosis implants disposed in the peritoneal cavity 118. The composition fluid 109 not only provides a short term local anaesthetic effect but also a long term cell membrane stabilizing effect on the leukocytes by the local anaesthetic reducing the release of cytokines and reducing dysmenorrhoea. The composition fluid 109 may also reduce the activity of and stabilize the cell membranes of the endometriosis implant cells also so that the implants may degenerate or regress. When the required amount has been applied, the cuff 108 is collapsed and the catheter 100 is withdrawn through the cervix 102 and the vagina 101.

While the present invention has been described in accordance with preferred compositions and embodiments, it is to be understood that certain substitutions and alterations may be made thereto without departing from the spirit and scope of the following claims.

I claim:

1. A process for reducing an activity level of endometriosis implants or peritoneal leukocytes in a woman, having a peritoneal cavity and a uterine cavity, to reduce dysmenorrhoea in the woman relative to the woman's present dysmenorrhoea, comprising:

mixing a compound which acts as a local anesthetic with a physiological salt to form a pharmaceutical composition comprising a pharmaceutically effective concentration of the local anesthetic with a pharmaceutically acceptable excipient;

placing the pharmaceutical composition into a catheter;

administering the pharmaceutical composition into the uterine cavity of the woman with the catheter to fill the uterine cavity with the pharmaceutical composition and permitting the pharmaceutical composition to overflow through fallopian tubes and into the peritoneal cavity; and depositing the pharmaceutical composition, flowing in the fallopian tubes, at a bottom of the peritoneal cavity in an amount of the pharmaceutical composition sufficient for reducing an activity level of the endometriosis implants or peritoneal leukocytes to reduce the woman's dysmenorrhoea.

2. A method for reducing an activity level of endometriosis implants or peritoneal leukocytes in a woman, having ovaries, peritoneal and uterine cavities, to reduce the woman's symptoms of premenstrual syndrome (PMS) relative to the woman's present PMS symptoms, comprising:

mixing a pharmaceutical combination compound comprising a local anesthetic with a physiological NaCl and a hyaluronan, placing the pharmaceutical combination compound in a catheter;

administering the pharmaceutical combination compound into the uterine cavity of the woman with the catheter to fill the uterine cavity with the pharmaceutical combination compound and permitting the pharmaceutical combination compound to overflow through fallopian tubes into the peritoneal cavity of the woman; and depositing the pharmaceutical combination compound into the peritoneal cavity in an amount of the pharmaceutical combination compound sufficient for reducing the activity level of the endometriosis implants or peritoneal leukocytes and for depressing a hormonal activity of the woman's ovaries to reduce the woman's PMS symptoms, the local anesthetic being selected from the group consisting of bupivacaine, lidocaine, mepivacaine, prilocaine and ropivacaine, wherein the combination composition comprises at least five micrograms/ml of the local anesthetic.

3. The method according to claim 2 wherein the step of administering comprises administering the pharmaceutical combination composition to the woman before ovulation of the woman.

4. A method for reducing an activity level of endometriosis implants or peritoneal leukocytes in a woman to reduce PMS symptoms in the woman relative to the woman's present PMS symptoms, comprising:

mixing a compound that acts as a local anesthetic with a physiological salt to form a pharmaceutical composition comprising a pharmaceutically effective concentration of the local anesthetic with a pharmaceutically acceptable excipient;

placing the pharmaceutical composition into a catheter;

administering the pharmaceutical composition into a uterine cavity of the woman with the catheter to fill the uterine cavity with the pharmaceutical composition and permitting the pharmaceutical composition to overflow from the uterine cavity through fallopian tubes and into the peritoneal cavity; and placing the pharmaceutical composition, flowing in the fallopian tubes, at a bottom of the peritoneal cavity in an amount of the pharmaceutical composition sufficient for reducing an activity level of the endometriosis implants or peritoneal leukocytes to reduce the woman's PMS symptoms.

* * * * *